US006641800B1

(12) United States Patent
Mistry et al.

(10) Patent No.: US 6,641,800 B1
(45) Date of Patent: *Nov. 4, 2003

(54) PRESSURIZED AEROSOL COMPOSITIONS COMPRISING POWDERED MEDICAMENT DISPERSED IN HYDROFLUOROALKANE

(75) Inventors: Suresh N Mistry, Birstall (GB); Mark Gibson, Shepshed (GB)

(73) Assignee: Fisons Ltd., West Malling (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/616,069

(22) Filed: Jul. 13, 2000

Related U.S. Application Data

(63) Continuation of application No. 08/478,338, filed on Jun. 7, 1995, now Pat. No. 6,123,924, which is a continuation of application No. 08/211,229, filed as application No. PCT/GB92/01749 on Sep. 23, 1992, now abandoned.

(30) Foreign Application Priority Data

Sep. 25, 1991 (GB) ............................................. 9120396
Sep. 28, 1991 (GB) ............................................. 9120675
Nov. 19, 1991 (GB) ............................................. 9124661
Feb. 14, 1992 (GB) ............................................. 9203212

(51) Int. Cl.$^7$ .......................... A61K 9/14; A61K 31/00; A61K 47/00
(52) U.S. Cl. .......................... 424/46; 424/45; 514/172; 514/177; 514/178; 514/179; 514/180; 514/182; 514/291; 514/314; 514/408; 514/428; 514/453; 514/456; 514/460; 514/529; 514/631; 514/636; 514/637; 514/642; 514/716; 514/717; 514/718; 514/721; 514/724; 514/727; 514/728; 514/731; 514/734; 514/738; 514/772; 514/772.3; 514/772.4; 514/772.5; 514/772.6; 514/772.7; 514/777; 514/783; 514/951; 514/958; 514/974

(58) Field of Search ................... 424/45, 46, 499, 424/501; 514/937, 172, 177, 178, 179, 180, 182, 291, 314, 408, 428, 453, 456, 460, 529, 631, 636, 637, 642, 716, 717, 718, 721, 724, 727, 728, 731, 734, 738, 772, 772.3, 772.4, 772.5, 772.6, 772.7, 777, 783, 951, 958, 974

(56) References Cited

U.S. PATENT DOCUMENTS

| 4,025,635 A | | 5/1977 | Hodson et al. |
| 4,752,466 A | | 6/1988 | Saferstein et al. |
| 4,869,899 A | | 9/1989 | Burghart et al. |
| 5,225,183 A | | 7/1993 | Purewal et al. |
| 5,605,674 A | | 2/1997 | Purewal et al. |
| 5,658,549 A | | 8/1997 | Akehurst et al. |
| 5,874,064 A | * | 2/1999 | Edwards et al. ............ 424/46 |
| 6,123,924 A | * | 9/2000 | Mistry ........................ 424/45 |

FOREIGN PATENT DOCUMENTS

| CH | 528270 | 5/1972 |
| EP | 372777 | 6/1990 |
| EP | 423695 | 4/1991 |
| WO | 86/01405 | 3/1986 |
| WO | 87/05210 | 9/1987 |
| WO | 87/05211 | 9/1987 |
| WO | 91/04011 | 4/1991 |
| WO | 91/11173 | 8/1991 |

* cited by examiner

Primary Examiner—Jose' G. Dees
Assistant Examiner—Frank Choi
(74) Attorney, Agent, or Firm—Nixon & Vanderhye

(57) ABSTRACT

Pressurized aerosol composition for administration by inhalation comprising a liquefied hydrofluoroalkane, a powdered medicament dispersed therein, and a suspending agent comprising a polymer soluble in the liquefied hydrofluoroalkane which is selected from polymers including recurring amide containing structural units, copolymers of amide containing units and carboxylic acid ester units, polyvinylacetate and acrylic acid/methacrylic acid ester copolymers.

32 Claims, No Drawings

PRESSURIZED AEROSOL COMPOSITIONS COMPRISING POWDERED MEDICAMENT DISPERSED IN HYDROFLUOROALKANE

This is a continuation of application Ser. No. 08/478,338, filed Jun. 7, 1995, now U.S. Pat. No. 6,123,924, which is a Rule 62 continuation of application Ser. No. 08/211,229, filed Aug. 3, 1994, now abandoned, which is a 371 of PCT/GB92/01749, filed Sep. 23, 1992, the entire contents of which are hereby incorporated by reference in this application.

This invention relates to pressurised aerosol compositions, in particular compositions of inhalation medicaments.

BACKGROUND OF THE INVENTION

Pressurized aerosols for the administration of medicaments, and indeed for other applications, conventionally contain one or more liquefied chlorofluorocarbons (CFC's) as propellant. Such materials are suitable for use in such applications since they have the right vapor pressures (or can be mixed in the right proportions to achieve a vapor pressure in the right range) and are essentially taste- and odor free.

In recent years there has been increasing concern about the depletion of the ozone layer in the upper atmosphere. This is believed to be due to the release into the atmosphere of CFC's and has led to a search for alternative agents for use in all applications of CFC's. To this end, aerosols for many applications are now pressurised using pressurised gases such as nitrogen or hydrocarbons. However, such propellants are generally not suitable for use in the administration of inhalation medicaments since they are toxic and/or the pressure within the canister falls each time the device is used which leads to unreproducible dosing.

The use of hydrofluorocarbons as aerosol propellants has also been suggested. However, considerable difficulties have been encountered in finding suspending agents which are soluble in hydrofluoroalkanes and capable of stabilising medicament suspensions.

SUMMARY OF THE INVENTION

Surprisingly, we have found that certain polymers are both soluble in the aerosol propellants and capable of stablizing medicament compositions.

DETAILED DESCRIPTION OF THE INVENTION

The polymer may be a homopolymer, that is the polymer consists of the same recurring structural units, or it may be a copolymer, that is the polymer contains recurring units in addition to either amide containing units or carboxylic acid ester units. The polymer may also be a copolymer of amide containing units and carboxylic acid ester units. Such copolymers may be either block copolymers or random copolymers.

We prefer polymers which include recurring structural units containing an amide group. We particularly prefer the amide containing unit to be 1-ethylene-pyrrolidin-2-one. We especially prefer the polymer to be a homopolymer containing recurring 1-ethylene-pyrrolidin-2-one, that is polyvinylpyrrolidone.

In general, we have found that polyvinylpyrrolidones having a wide range of average molecular weights give acceptable suspensions. Although polymers can be characterised by their weight average molecular weights, viscosity average molecular weights or number average molecular weights, it is more usual to characterise polymers, in particular polymers such as polyvinylpyrrolidone, by K values, in which K is determined from viscosity measurements using the Fikentscher equation (H. Fikentscher, *Cellusochemie*, 1932, 13, 58–64 and 71–74). In particular we prefer the polymer to have a K value of from 10 to 150, more preferably 15 to 120. Particular is K values and ranges that may be mentioned include 10–14, 15–18, 29–32, 88–100 and 115–125.

Suitable polymers containing carboxylic acid ester containing recurring structural units include polyvinylacetate and copolymers of vinyl acetate and vinyl pyrrolidone, that is polyvinylpyrrolidone/vinyl acetate copolymer. We have found that polyvinylacetate with a weight average molecular weight of 250,000 gives particularly stable suspensions.

Other polymers that may be mentioned include acrylic acid/methacrylic acid ester copolymers, especially those in which the methyl and ethyl ester groups have been replaced with a low content of trimethylammoniumethyl groups, preferably at a ratio of 1:20, especially at a ratio of 1:40. We have found that such copolymers having a weight average molecular weight of 150,000 give stable suspensions.

The amount of polymer in the composition will depend on the active ingredient to be dispersed, its concentration and the particular polymer selected. However, in general the amount of polymer is from 0.00001 to 10% w/w, more preferably 0.0001 to 5% w/w and especially 0.001 to 1% w/w.

The compositions may, in addition to the polymer, contain other excipients, in particular excipients intended to improve valve lubrication and excipients to modify flavour. Particular lubricants that may be mentioned include polyethoxylated compounds, especially polyethylene glycol. We prefer polyethylene glycol having a mean molecular weight of from 200 to 3000, preferably 400 to 2000, eg 1500. Other polyethoxylated compounds that may be used as lubricants include polysorbates, eg polysorbate 80, and alkyl aryl polyether alcohols, eg tyloxapol. Other lubricating excipients that may be mentioned include high molecular weight fully halogenated chlorofluorocarbons and esters of medium chain fatty acids. The amount of lubricant in the composition will depend on the other components of the composition, the active ingredient, the nature of the valve, etc. In general, we prefer a concentration of 0.01 to 4% w/w and more preferably 0.1 to 2% w/w.

Flavour modifying excipients that may be added to the composition include peppermint oil, menthol, Dentomint (Dentomint is a tradename), saccharin and saccharin sodium. When the flavour modifying excipient is a solid, preferably it is micronised. The concentration will depend on the individual composition and the flavour modifying excipient. In general, we prefer a concentration of 0.005 to 4% w/w; more preferably 0.01 to 1% w/w.

By the term 'hydrofluoroalkane' we mean a compound of general formula $$C_xH_yF_z$$

in which x is an integer from 1 to 3, y+z=2x+2 and y and z are both at least 1.

Particular hydrofluoroalkanes of interest are $CF_3CFH_2$ (Propellant 134a), $CH_3CHF_2$ (Propellant 152a) and $CF_3CHFCF_3$ (Propellant 227). We particularly prefer compositions including propellant 227.

In general the vapour pressure of the propellant mixture should be in the range suitable and permitted for aerosol propellants. The vapour pressure may be varied by mixing one or more hydrofluoroalkanes and/or some other suitable vapour pressure modifying agent in appropriate proportions.

We prefer the vapour pressure of the mixture to be in the range 20 to 100 psig, more preferably 40 to 80 psig, eg about 60 psig.

In certain cases we have found it advantageous to add to the compositions excipients capable of increasing the solubility of the polymer or of other excipients, in the propellant. In general we have found that the polymers selected have a solubility in the propellant of at least 0.0001% w/w, preferably at least 0.001% w/w, particularly 0.01% w/w and especially 0.1% w/w. Excipients capable of increasing the solubility of the polymer include liquid excipients which are more polar than the liquefied propellant, where polarity is defined in terms of relative Kauri butanol values, as described in European patent application 0 372 777. Particular excipients that may be mentioned include alcohols eg ethanol and isopropanol. However, in contrast to the teaching of EP 0 372 777, we have found that only very small quantities of such excipients are required. In particular we have found that good compositions can be prepared in propellant 134a with polyvinylpyrrolidone as polymer with a variety of active ingredients and less than 10% w/w, preferably less than 5% w/w, more preferably less than 2% w/w, eg 0.2% w/w ethanol.

Medicaments which may be dispersed in the propellant mixture according to the invention include any medicaments which are conventionally administered to the lung and/or nose by inhalation of a pressurised aerosol formulation. Such medicaments include drugs for use in the prophylactic or remedial treatment of reversible obstructive airways disease, eg drugs such as sodium cromoglycate, nedocromil sodium, inhaled steroids, eg beclomethasone dipropionate, fluticasone propionate, budesonide and tipredane, and bronchodilators, eg salbutamol, reproterol, terbutaline, formoterol, pirbuterol, isoprenaline, salmeterol, fenoterol and salts thereof, and anticholinergic agents such as ipratropium bromide, oxitropium bromide and atropine and combinations of two or more of these agents, eg a combination of a prophylactic agent with a bronchodilator, eg sodium cromoglycate with salbutamol.

Other medicaments that may be mentioned include antihistamine; eg clemastine, pentamidine and salts thereof, acetyl-β-methylcholine bromide, peptide hormones such as insulin and amylin, bradykinin antagonists, $PLA_2$ inhibitors, PAF antagonists, lipoxygenase inhibitors, leukotriene antagonists CNS active drugs, such as NMDA antagonists, glutamate antagonists, CCK agonists and antagonists; macrolide compounds including FK 506, rapamycin, cyclosporin and structurally related compounds, vitamins, vaccines, eg MMR vaccine and polio vaccine and vectors for gene therapy, eg plasmids containing genes intended to correct genetic disorders such as cystic fibrosis.

Where the medicament is intended for delivery to the lung, it preferably has a particle size distribution such that a high proportion of the particles are of a size capable of penetrating deep into the lung. In particular, the medicament is preferably in a form having a mass median diameter of from 0.01 to 10 µm, More preferably from 0.1 to 4 µm, eg about 2 or 3 µm.

The amount of medicament in the composition will depend on the nature of the active ingredient and the condition to be treated. However, the composition preferably comprises from 0.01 to 15% w/w, preferably from 0.1 to 10% w/w, and most preferably from 0.5 to 5% w/w medicament.

According to a further aspect of the invention there is provided a method of producing a pressurised aerosol composition as herein described, which comprises dispersing the powdered medicament and the polymer in the liquefied hydrofluoroalkane.

In particular, the compositions may be produced by cold fill or pressure fill techniques. In cold filling, the ingredients are placed in a cooled mixing vessel, cooled liquefied propellant added and a dispersion produced by vigorous stirring. Alternatively, a slurry may be prepared of the ingredients in a portion of cooled liquid propellant and the remainder of the liquefied propellant added under vigorous stirring. Aliquots of the dispersed composition are then filled into cooled aerosol cans and sealed with a suitable valve, eg a metering valve.

In pressure filling, the ingredients are placed in a pressure vessel, liquefied propellant added under pressure through a valve and a dispersion of the ingredients in the liquefied dispersed composition are then filled, under pressure, through the valve into suitable cans provided with appropriate valves, eg metering valves.

The compositions according to the invention are advantageous in that the solubility of the polymer is such as to ensure good dispersion of the medicament and smooth operation of the aerosol valve.

The compositions of the present invention may also be advantageous in that they are substantially taste- and odour-free and have suitable vapour pressures for the administration of medicaments by inhalation, yet are environmentally safe and acceptable, especially when compared with compositions including chlorofluorocarbons. In addition, they may be less irritant than corresponding compositions including conventional surfactants such as oleic acid and sorbitan trioleate.

The performance of the compositions according to the present invention can be assessed using the following test procedures:

1. Settling Times

A glass bottle containing the composition is gently shaken five times and then stood upright. The time interval between standing the bottle upright and the first appearance of flocculation or separation of powder in the propellant determined ($S_1$). Timing is continued until complete separation, defined as when three lines of standard newspaper print can be read through the propellant from the top or bottom, depending on whether the active ingredient floats or sinks ($S_2$). In some compositions, complete separation does not occur. For these compositions, a turbidity factor ranging from 1 to 5 is determined, 1 denoting that a small proportion so of the active ingredient is suspended and 5 denoting that the majority of the active ingredient is suspended.

2. Dispersion Tests

Dispersion testing on compositions formulated in cans having a metering valve can be assessed using a glass multistage liquid impinger, eg of the type described by J. H. Bell el al, *J. Pharm. Sci.*, 1971, 60(10), 1559.

3. Lubrication

The lubricating effects of the composition can be assessed by filling the formulation into a can and closing the can with a modified metering valve from which the return spring has been removed. The stem of the valve is subjected to a compression force and the reading recorded in Newtons. This gives a measure of the lubricating efficacy of the composition.

4. Dose Uniformity

Dose uniformity is assessed by discharging a metered dose aerosol can containing the composition into a filter tube which has sufficient air flowing through it to entrain all the dose. The tube is washed out with a suitable solvent and the amount of medicament assayed. The medicament entrained on the mouthpiece is also washed off and assayed. The variation of dose evaluated throughout the life of the can is a measure of dose uniformity. In a variation of this test, dose uniformity after standing can be assessed by shaking the aerosol can, allowing to stand for a predetermined time and assessing dose in the manner described above.

5. Caking Potential

Compositions to be assessed are filled into plastic coated glass bottles. The assessment is carried out by allowing the samples to be stored for a period of time in order that complete sedimentation and compaction of the powder mass can take place, eg 3 months. After that period, the glass bottles are shaken by gentle twisting of the hand to totally invert the bottles. The number of bottle inversions required to completely resuspend the drug is noted. The number gives a measure of the degree of compaction of the composition. Since ease of drug particle redispersion is essential for dose uniformity, any composition requiring more than 5 shakes suggests possible problems in long-term storage.

The invention will now be illustrated, but in no way limited, by the following Examples.

EXAMPLES

Method

The required amounts of micronised active ingredient, suspending agent and other excipients, were weighed into plastic coated glass bottles and crimped with an appropriate valve. The desired amount of liquefied propellant was then transferred using a transfer button and the contents of the bottle sonicated to ensure thorough mixing. Unless otherwise stated, the fill volume for the bottles was 20 ml.

Materials

Active Ingredients

All active ingredients were micronised. In general, the active ingredients were anhydrous, although nedocromil sodium and sodium cromoglycate were used in their equilibrium hydrated form which each contain about 10% w/w water at room temperature.

Polyethyleneglycols (PEG)

The average molecular weight of the polyethyleneglycol used is indicated by the number 200, 400, etc following PEG.

Halocarbon Oil

Halocarbon oil is the proprietary name given to a series of high molecular weight fully halogenated chlorofluorocarbons of chlorotrifluoroethylene telomers obtainable from Halocarbon Products Corporation, New Jersey, USA.

Miglyols

Miglyol® Neutral Oils

Miglyol® neutral oils are esters of medium chain fatty acids and are sometimes referred to as fractionated coconut oils. Miglyol is a trademark of Hüls AG. The following oils were used.

Miglyole® 810

A triglyceride of fractionated $C_8/C_{10}$ coconut oil fatty acids classified by the CTFA as caprylic/capric triglyceride. It meets the requirements of the British Pharmacopoeia 1988 for the monograph "Fractionated Coconut Oil". It is a low viscosity oil of neutral taste and smell, with a turbidity point below 0° C.

Miglyol® 829

A glyceryl ester of fractionated $C_8/C_{10}$ coconut fatty acids linked to succinic acid and is classified by the CTFA as caprylic/capric/diglyceryl succinate. It has a turbidity point below −30° C., is soluble in alcohol, has a viscosity of approximately 250 mPa.s and a density of approximately 1.

Miglyol® 840

A propylene glycol diester of saturated vegetable fatty acids with $C_8/C_{10}$ chain lengths, classified by the CFTA as propyleneglycol dicaprylate/dicaprate. It meets the requirements of the German Pharmacopoeia, DAR9, 1st supplement, for the monograph "Propyleneglycoloctanoatodecanoate". It has a turbidity point below −30° C. and is soluble in 90% ethanol.

Polyvinylpyrrolidones

All polyvinylpyrrolidones used were essentially linear homopolymers formed by the free radical polynerisation of N-vinylpyrrolidone. PVP(K29/32), PVP(K90), PVP(K120), PVP(C15) and PVP(C30) refer to the polyvinylpyrrolidones obtainable from GAF Chemical Corporation and sold under the Trade Mark PLASDONE®. PVP/17PF refers to KOLLIDON 17PF, a polyvinylpyrrolidone available from BASF (KOLLIDON is a registered Trade Mark).

The manufacturing processes for polyyinylpyrrolidone and the other polymers used herein produce polymer mixtures containing molecules of unequal chain length and thus different molecular weights. Such polymers are usually characterised by their K values, in which K is determined from viscosity measurements using the Fikentscher equation (H. Fikentscher, *Cellusochemie*, 1932, 13, 58–64 and 71–74). The polymers can also be characterised by their average molecular weights ($\overline{M}w$), viscosity average molecular weights ($\overline{M}v$) and number average molecular weights ($\overline{M}n$).

Characterising data for the polyvinylpyrrolidones used were as follows:

|        | K        | $\overline{M}w$ | $\overline{M}v$ | $\overline{M}n$ |
|--------|----------|-----------|-----------|-------|
| PVP 17 PF | 15–18    | 9000      | —         | 2500  |
| K29/32 | 29–32    | —         | —         | —     |
| K90    | 94 ± 6   | 1,280,000 | 63000     | —     |
| K120   | 120 ± 5  | 2,800,000 | 1,450,000 | —     |
| C15    | 17 ± 1   | 10500     | 7000      | 3000  |
| C30    | 30.5 ± 1 | 62500     | 3800      | 16500 |

Polyvinylpyrrolidone/vinylacetate Copolymers

Polyvinylpyrrolidone/vinylacetate copolymers are obtainable from GAF Chemical Corporation. The E- and I- series of PVP/VA copolymers were supplied as 50% solutions in ethanol and isopropanol respectively. S-630 refers to the white, spray dried polymer of PVP/VA having the characteristics set out below. Characterising data for PVP/VA used:

|        |       | K value | VP/VA ratio |
|--------|-------|---------|-------------|
| PVP/VA | S-630 | 30–50   | 60/40       |
|        | E-535 | 30–50   | 50/50       |
|        | I-535 | 25–35   | 50/50       |
|        | E-335 | 25–35   | 30/70       |

Acrylic Acid/metbacrylic Acid Ester Copolymers

The acrylic acid/methacrylic acid ester copolymers used were copolymers synthesized from acrylic and methacrylic acid ethyl and methyl esters with a low content of quaternary ammonium groups. The molar ratio of these ammonium group to the neutral (meth)acrylic acid esters is 1:40. The weight average molecular weight is approximately 150000. The polymer used was EUDRAGIT RS PM, obtainable from Röhn Pharma GmbH. (EUDRAGIT is a registered Trade Mark).

Polyvinylacetate

The polyvinylacetate used had a weight average molecular weight of about 26,000.

A. Compositions Containing Polyvinylpyrrolidone and Propellant 227

The following active ingredients were formulated at the concentration shown with PVP in propellant 227 PLASDONE C30 (PLASDONE is a registered Trade Mark of GAF Chemicals Corporation).

| a) | with 0.05% w/w PVP(C-30) | |
|---|---|---|
| 1. | Terbutaline sulphate | 5 mg/ml |
| 2. | Beclometbasone dipropionate | 5 mg/ml |
| 3. | Salbutamol sulphate | 4 mg/ml |
| 4. | Fluticasone propionate | 4 mg/ml |
| 5. | Reproterol hydrochloride | 10 mg/ml |
| 6. | Fenoterol hydrobromide | 4 mg/ml |
| 7. | Sodium cromoglycate | 10 mg/ml |
| 8. | Sodium cromoglycate | 50 mg/ml |
| 9. | Ipratropium bromide | 0.8 mg/ml |
| 10. | Pentamidine isoethionate | 4 mg/ml |
| 11. | Clemastine | 4 mg/ml |
| 12. | Acetyl-β-methylcholine bromide | 10 mg/ml |
| 13. | Budesonide | 4 mg/ml |
| b) | with 0.1% w/v PVP(17PF) | |
| 1. | Fenoterol hydrobromide | 4 mg/ml |
| 2. | Terbutaline sulphate | 5 mg/ml |
| 3. | Salbutamol sulphate | 4 mg/ml |
| c) | with 0.025% w/v PVP(C30) | |
| 1. | Tipredane | 10 mg/ml |

B. Compositions Containing Polyvinylpyrrolidone/vinyl Acetate Copolymer in Propellant 227

The following active ingredients were formulated in propellant 227 at the concentrations shown.

| a) | with 0.05% w/v PVP/PVA S-630 | |
|---|---|---|
| 1. | Terbutaline sulphate | 5 mg/ml |
| 2. | Beclometbasone dipropionate | 5 mg/ml |
| 3. | Salbutamol sulphate | 4 mg/ml |
| 4. | Fluticasone propionate | 4 mg/ml |
| 5. | Reproterol hydrochloride | 10 mg/ml |
| 6. | Fenoterol hydrobromide | 4 mg/ml |
| 7. | Sodium cromoglycate | 10 mg/ml |
| 8. | Sodium cromoglycate | 50 mg/ml |
| 9. | Ipratropium bromide | 0.8 mg/ml |
| 10. | Acetyl-β-methylcholine bromide | 10 mg/ml |
| 11. | Budesonide | 4 mg/ml |
| b) | with 0.025% w/v PVP/VA S-630 | |
| 1. | Tipredane | 10 mg/ml |

C. Compositions Containing PVP or PVP/VA, Propellant 227 and Polyethylene Glycol The following active ingredients were formulated in propellant 227 at the concentration shown with 0.5% w/v PEG600.

| a) | with 0.05% w/v PVP(C30) | |
|---|---|---|
| 1. | Salbutamol sulphate | 4 mg/ml |
| 2. | Sodium cromoglycate | 50 mg/ml |
| 3. | Reproterol hydrochloride | 10 mg/ml |
| b) | with 0.05% w/v PVP/VA S-630 | |
| 1. | Salbutamol sulphate | 4 mg/ml |
| 2. | Sodium cromoglycate | 50 mg/ml |
| 3. | Reproterol hydrochloride | 10 mg/ml |
| 4. | Budesonide | 4 mg/ml |
| c) | with 0.1% w/v PVP(17PF) | |
| 1. | Terbutaline sulphate | 5 mg/ml |
| 2. | Fenoterol hydrobromide | 4 mg/ml |

D. Compositions Containing Acrylic Acid/methacrylic Acid Ester Copolymers and Propellant 227

The following active ingredients were formulated at the concentration shown with 0.1% w/v EUDRAGIT RS (EUDRAGIT is a Trade Mark of Röhn Pharma GmbH) in propellant 227.

| a) | 1. | Terbutaline | 5 mg/ml |
|---|---|---|---|
| | 2. | Beclomethasone dipropionate | 5 mg/ml |
| | 3. | Salbutamol sulphate | 4 mg/ml |
| | 4. | Fluticasone | 4 mg/ml |
| | 5. | Reproterol hydrochloride | 10 mg/ml |
| | 6. | Fenoterol | 4mg/ml |
| | 7. | Sodium cromoglycate | 10 mg/ml |
| | 8. | Ipratropium bromide | 0.8 mg/ml |
| | 9. | Clemastine | 4 mg/ml |
| | 10. | Acetyl-p-methylcholine bromide | 10 mg/ml |
| b) | compositions including 0.5% w/w PEG 600 | | |
| | 11. | Beclomethasone dipropionate | 5 mg/ml |
| | 12. | Sodium cromoglycate | 50 mg/ml |
| | 13. | Reproterol hydrochloride | 10 mg/ml |
| | 14. | Fenoterol hydrobromide | 4 mg/ml |

E. Compositions in Propellant 134a

The following active ingredients were formulated at the concentration shown in propellant 134a.

| 1. | Tipredane | 10 mg/ml |
|---|---|---|
| | PVP(C30) | 0.1% w/w |
| | ethanol | 5.0% w/w |
| 2. | Tipredane | 10 mg/ml |
| | PVP(C30) | 0.1% w/w |
| | ethanol | 10.0% w/w |
| 3. | Nedocromil sodium | 20 mg/ml |
| | PVP(C30) | 0.1% w/w |
| | ethanol | 5.0% w/w |
| 4. | Nedocromil sodium | 20 mg/ml |
| | PVP(C30) | 0.1% w/w |
| | ethanol | 10.0% w/w |
| 5. | Tipredane | 10 mg/ml |
| | PVP/VA S-630 | 0.1% w/w |
| | ethanol | 5.0% w/w |
| 6. | Tipredane | 10 mg/ml |
| | PVP(C30) | 0.25% w/w |
| | ethanol | 5.0% w/w |
| 7. | Tipredane | 10 mg/ml |
| | PVP(C30) | 0.5% w/w |
| | ethanol | 5.0% w/w |
| 8. | Nedocromil sodium | 20 mg/ml |
| | PVP/VA S-630 | 0.1% w/w |
| | ethanol | 5.0% w/w |

|     |                        |              |
| --- | ---------------------- | ------------ |
| 9.  | Nedocromil sodium      | 20 mg/ml     |
|     | PVP/C30                | 0.25% w/w    |
|     | ethanol                | 5.0% w/w     |
| 10. | Nedocromil sodium      | 20 mg/ml     |
|     | PVP(C30)               | 0.5% w/w     |
|     | ethanol                | 5.0% w/w     |
| 11. | Tipredane              | 10 mg/ml     |
|     | PVP(C30)               | 0.1% w/w     |
|     | PEG 600                | 0.5% w/w     |
|     | ethanol                | 5.0% w/w     |
| 12. | Tipredane              | 10 mg/ml     |
|     | PVP(C30)               | 0.1% w/w     |
|     | PEG 600                | 0.5% w/w     |
|     | ethanol                | 10.0% w/w    |
| 13. | Nedocromil sodium      | 20 mg/ml     |
|     | PVP(C30)               | 0.1% w/w     |
|     | PEG 600                | 0.5% w/w     |
|     | ethanol                | 5.0% w/w     |
| 14. | Nedocromil sodium      | 20 mg/ml     |
|     | PVP(C30)               | 0.1% w/w     |
|     | PEG 600                | 0.5% w/w     |
|     | ethanol                | 10.0% w/w    |
| 15. | Nedocromil sodium      | 20 mg/ml     |
|     | PVP(C30)               | 0.05% w/w    |
|     | PEG 600                | 0.5% w/w     |
|     | ethanol                | 0.2% w/w     |
| 16. | Beclomethasone         | 5 mg/ml      |
|     | dipropionate           |              |
|     | PVP/VA S-630           | 0.1% w/w     |
|     | ethanol                | 2.0% w/w     |
| 17. | Beclomethasone         | 5 mg/ml      |
|     | dipropionate           |              |
|     | PVP/VA S-630           | 0.1% w/w     |
|     | ethanol                | 5.0% w/w     |
| 18. | Beclomethasone         | 5 mg/ml      |
|     | dipropionate           |              |
|     | PVP(C30)               | 0.1% w/w     |
|     | ethanol                | 5.0% w/w     |

F. Compositions Containing Polyvinylacetate

|     |                   |              |
| --- | ----------------- | ------------ |
| a)  | In propellant 134a |             |
| 1.  | Tipredane         | 10 mg/ml     |
|     | Polyvinylacetate  | 0.042% w/w   |
|     | Nedocromil sodium | 20 mg/ml     |
|     | Polyvinylacetate  | 0.042% w/w   |
| b)  | In propellant 227 |              |
| 1.  | Tipredane         | 10 mg/ml     |
|     | Polyvinylacetate  | 0.035% w/w   |
|     | Nedocromil sodium | 20 mg/ml     |
| 2.  | Polyvinylacetate  | 0.035% w/w   |

G. Compositions Using Polyvinylpyrrolidone of Different K Values

The following active ingredients were formulated in propellant 227 at the concentrations shown, with 0.1% w/w polyvinylpyrrolidone having the K value shown:

|     |                       |          |
| --- | --------------------- | -------- |
| a)  | PVP(K29/32)           |          |
| 1.  | Tipredane             | 10 mg/ml |
| 2.  | Nedocromil sodium     | 20 mg/ml |
| 3.  | Sodium cromoglycate   | 20 mg/ml |
| 4.  | Reproterol hydrochloride | 4 mg/ml |
| 5.  | Salbutamol sulphate   | 4 mg/ml  |
| b)  | PVP(K90)              |          |
| 1.  | Tipredane             | 10 mg/ml |
| 2.  | Nedocromil sodium     | 20 mg/ml |
| c)  | PVP(K120)             |          |
| 1.  | Tipredane             | 10 mg/ml |
| 2.  | Nedocromil sodium     | 20 mg/ml |
| d)  | PVP(C15)              |          |
| 1.  | Tipredane             | 10 mg/ml |
| 2.  | Nedocromil sodium     | 20 mg/ml |

H. Compositions Using Polyvinylpyrrolidone/vinylacetate Copolymers of Different Vinylpyrrolidone/vinylacetate Ratios Tipredane and nedocromil sodium were formulated in propellant 227 at the concentrations shown, with 0.1% w/w PVP/VA having the vinylpyrrolidone/vinylacetate ratio shown.

|     |                        |          |
| --- | ---------------------- | -------- |
| a)  | Nedocromil sodium 20 mg/ml |      |
| 1.  | PVP/VA E-535           | (50/50)  |
| 2.  | PVP/VA I-535           | (50/50)  |
| 3.  | PVP/VA E-335           | (30/70)  |
| b)  | Tipredane 10 mg/ml     |          |
| 1.  | PVP/VA E-535           | (50/50)  |
| 2.  | PVP/VA I-535           | (50/50)  |
| 3.  | PVP/VA E-335           | (30/70)  |

Further Tipredane Formulations

| Ex | Tipredane (mg/ml) | PVP/VA S-630 % w/w | PVP/C30 % w/w | Propellant |
| --- | --- | --- | --- | --- |
| 1  | 4  | 0.0025 | — | 134a |
| 2  | 4  | 0.01   | — | 134a |
| 3  | 4  | 0.025  | — | 134a |
| 4  | 4  | 0.05   | — | 134a |
| 5  | 10 | 0.0025 | — | 134a |
| 6  | 10 | 0.01   | — | 134a |
| 7  | 10 | 0.025  | — | 134a |
| 8  | 10 | 0.05   | — | 134a |
| 9  | 30 | 0.0025 | — | 134a |
| 10 | 30 | 0.01   | — | 134a |
| 11 | 30 | 0.025  | — | 134a |
| 12 | 30 | 0.05   | — | 134a |
| 13 | 4  | 0.0025 | — | 227  |
| 14 | 4  | 0.01   | — | 227  |
| 15 | 4  | 0.025  | — | 227  |
| 16 | 4  | 0.05   | — | 227  |
| 17 | 10 | 0.0025 | — | 227  |
| 18 | 10 | 0.01   | — | 227  |
| 19 | 10 | 0.025  | — | 227  |
| 20 | 10 | 0.05   | — | 227  |
| 21 | 30 | 0.0025 | — | 227  |
| 22 | 30 | 0.01   | — | 227  |
| 23 | 30 | 0.025  | — | 227  |
| 24 | 30 | 0.05   | — | 227  |
| 25 | 4  | —      | 0.0025 | 134a |
| 26 | 4  | —      | 0.01   | 134a |
| 27 | 4  | —      | 0.025  | 134a |
| 28 | 4  | —      | 0.05   | 134a |
| 29 | 10 | —      | 0.0025 | 134a |
| 30 | 10 | —      | 0.01   | 134a |
| 31 | 10 | —      | 0.025  | 134a |
| 32 | 10 | —      | 0.05   | 134a |

-continued

| Ex | Tipredane (mg/ml) | PVP/VA S-630 % w/w | PVP/C30 % w/w | Propellant |
|---|---|---|---|---|
| 33 | 30 | — | 0.0025 | 134a |
| 34 | 30 | — | 0.01 | 134a |
| 35 | 30 | — | 0.025 | 134a |
| 36 | 30 | — | 0.05 | 134a |
| 37 | 4 | — | 0.0025 | 227 |
| 38 | 4 | — | 0.01 | 227 |
| 39 | 4 | — | 0.025 | 227 |
| 40 | 4 | — | 0.05 | 227 |
| 41 | 10 | — | 0.0025 | 227 |
| 42 | 10 | — | 0.01 | 227 |
| 43 | 10 | — | 0.025 | 227 |
| 44 | 10 | — | 0.05 | 227 |
| 45 | 30 | — | 0.0025 | 227 |
| 46 | 30 | — | 0.01 | 227 |
| 47 | 30 | — | 0.025 | 227 |
| 48 | 30 | — | 0.05 | 227 |

J. Compositions Containing Flavouring Agents

The following compositions were made up in propellant 227, with 0.1% w/w PVP/VA S-630.

| 1. | Nedocromil sodium | 20 mg/ml |
| | peppermint oil | 0.1% w/w |
| 2. | Nedocromil sodium | 20 mg/ml |
| | menthol | 0.05% w/w |
| | saccharin | 0.03% w/w |
| 3. | Tipredane | 10 mg/ml |
| | menthol | 0.05% w/w |
| | saccharin | 0.03% w/w |

K. Compositions Containing Additional Excipients

The following composition was made up in propellant 227, to examine the effects of different excipients as valve lubricants.

| a) | Nedocromil sodium | 20 mg/ml |
| | PVP/C30 | 0.1% w/w |
| | Lubricant | 0.5% w/w |
| | Menthol | 0.05% w/w |
| | Saccharin, micronised | 0.03% w/w |
| | Lubricants: | |
| | PEG 200 | |
| | PEG 400 | |
| | PEG 600 | |
| | PEG 1000 | |
| | Miglyol 810 | |
| | Miglyol 829 | |
| | Miglyol 840 | |
| | Ethyl oleate | |
| | Halocarbon oil 27 | |
| | Tyloxapol | |
| | Polysorbate 80 | |
| b) | Nedocromil sodium | 20 mg/ml |
| | PVP (C30) | 0.10% w/w |
| | PEG 1500 | 0.20% w/w |
| | Menthol | 0.05% w/w |
| | Saccharin, micronised | 0.03% w/w |
| c) | Tipredane | 10.0 mg/ml |
| | PVP (C30) | 0.10% w/w |
| | Lubricant | 0.50% w/w |
| | Lubricants: PEG 600 | |
| | PEG 1000 | |
| d) | Tipredane | 10.0 mg/ml |
| | PVP (C30) | 0.10% w/w |

| | Lubricant | 0.20% w/w |
| | Lubricants: | PEG 600 |
| | | PEG 1000 |
| | | PEG 1500 |

What is claimed is:

1. A pressurized suspension aerosol composition comprising a liquefied hydrofluoroalkane, a powdered medicament dispersed therein, wherein the medicament particles in said powdered medicament have a mass median diameter of 0.01 to 10 microns, and a suspending agent comprising a polymer soluble in the liquefied hydrofluoroalkane, said polymer being present in an amount of 0.00001 to 10% w/w, said polymer being different from said powdered medicament and being selected from the group consisting of polymers including recurring 1-ethylene-pyrrolidin-2-one units, copolymers of 1-ethylene-pyrrolidin-2-one units and vinylacetate units, polyvinylacetate and acrylic acid/methacrylic acid ester copolymers, and wherein said aerosol composition is for administration by inhalation.

2. The composition according to claim 1 wherein the polymer includes recurring 1-ethylene-pyrrolidin-2-one units.

3. The composition according to claim 1 wherein the polymer is polyvinylpyrrolidone.

4. The composition according to claim 1 wherein the polymer is a copolymer containing recurring 1-ethylene-pyrrolidin-2-one units.

5. The composition according to claim 1 wherein the polymer is polyvinylpyrrolidone/vinyl acetate copolymer.

6. The composition according to claim 1 wherein the polymer is polyvinylacetate or a copolymer of acrylic acid and methacrylic acid esters.

7. The composition according to claim 1 which contains less than 10% w/w of excipients capable of increasing the solubility of the polymer in the hydrofluoroalkane.

8. The composition according to claim 1 which contains less than 5% w/w of excipients capable of increasing the solubility of the polymer in the hydrofluoroalkane.

9. The composition according to claim 1 which contains less than 10% w/w of ethanol.

10. The composition according to claim 1 which contains less than 5% w/w of ethanol.

11. The composition according to claim 1 which contains an excipient which acts as a valve lubricant.

12. The composition according to claim 1 which contains a flavor modifying excipient.

13. The composition according to claim 1 which contains a flavor modifying excipient and an excipient which acts as a valve lubricant.

14. The composition according to claim 1 wherein the excipient which acts as a valve lubricant comprises polyethylene glycol.

15. The composition according to claim 14 wherein the polyethylene glycol has a mean molecular weight of from 200 to 3000.

16. The composition according to claim 15 wherein the polyethylene glycol has a mean molecular weight of from 400 to 2000.

17. The composition according to claim 1 wherein the excipient which acts as a valve lubricant, is present at a concentration of between 0.01 to 4% w/w.

18. The composition according to claim 17 wherein the excipient which acts as a valve lubricant is present at a concentration of between 0.1 to 2% w/w.

19. The composition according to claim 1 wherein the flavor modifying excipient comprises one or more of peppermint oil, menthol, saccharin or saccharin sodium.

20. The composition according to claim 1 wherein the hydrofluoroalkane is $CF_3CHFCF_3$.

21. The composition according to claim 1, wherein the medicament is selected from the group consisting of terbutaline sulphate, beclomethasone dipropionate, salbutamol sulphate, fluticasone propionate, reproterol hydrochloride, fenoterol hydrobromide, sodium cromoglycate, nedocromil sodium, tipredane, pentamidine isethionate, clemastine, acetyl-β-methylcholine bromide and budesonide.

22. The composition according to claim 1 wherein the concentration of medicament is from 0.01 to 15% w/w.

23. The composition according to claim 1 wherein the hydrofluoroalkane is $CF_3CHFCF_3$ and the polymer includes recurring 1-ethylene-pyrrolidin-2-one units.

24. The composition according to claim 23 wherein the polymer is polyvinylpyrrolidone.

25. The composition according to claim 24 which contains less than 10% w/w of ethanol.

26. The composition according to claim 24 which contains less than 5% w/w of ethanol.

27. The composition according to claim 26 which contains polyethylene glycol.

28. The composition according to claim 24 which contains polyethylene glycol.

29. The composition according to claim 23 which contains less than 10% w/w of ethanol.

30. The composition according to claim 23 which contains less than 5% w/w of ethanol.

31. The composition according to claim 23 which contains polyethylene glycol.

32. A process for the preparation of a composition according to claim 1, which comprises dispersing the powdered medicament and the suspending agent in the liquefied hydrofluoroalkane.

* * * * *